United States Patent [19]

Harada et al.

[11] Patent Number: 4,915,814
[45] Date of Patent: Apr. 10, 1990

[54] SENSOR FOR MEASUREMENT OF AIR/FUEL RATIO AND METHOD OF MANUFACTURING

[75] Inventors: Takeshi Harada; Masatoshi Kanamaru, both of Ibaraki; Yoshiro Ibaraki, Tsukuba; Katsuyoshi Terakado, Ibaraki; Sadayasu Ueno, Katsuta; Norio Ichikawa, Mito, all of Japan

[73] Assignee: Hitachi, Ltd., Tokyo, Japan

[21] Appl. No.: 250,238

[22] Filed: Sep. 28, 1988

[30] Foreign Application Priority Data

Sep. 30, 1987 [JP] Japan ............................... 62-243684
Feb. 10, 1988 [JP] Japan ............................... 63-27518
Feb. 29, 1988 [JP] Japan ............................... 63-44405

[51] Int. Cl.$^4$ ................. G01N 27/56; G01N 27/58; B05D 5/12
[52] U.S. Cl. ........................... 204/425; 204/428; 204/429; 427/126.2; 427/126.3
[58] Field of Search ............... 204/412, 424, 425, 426, 204/427, 428, 429; 427/126.1, 126.2, 126.3, 126.4

[56] References Cited

U.S. PATENT DOCUMENTS

| | | | |
|---|---|---|---|
| 4,021,326 | 5/1977 | Pollner et al. | 204/429 |
| 4,164,462 | 8/1979 | Ichikawa et al. | 204/429 |
| 4,356,065 | 10/1982 | Dietz | 204/1 T |
| 4,383,906 | 5/1983 | Sano et al. | 204/429 X |
| 4,402,820 | 9/1983 | Sano et al. | 204/429 X |
| 4,476,008 | 10/1984 | Sano et al. | 204/429 X |
| 4,502,939 | 3/1985 | Holfelder et al. | 204/429 |

FOREIGN PATENT DOCUMENTS 53-13980 2/1978 Japan .

OTHER PUBLICATIONS

National Technical Report, vol. 26 (1980), pp. 457-465.
Kogyozairyo, vol. 31 (1983), pp. 50-54.

Primary Examiner—Nam X. Nguyen
Attorney, Agent, or Firm—Antonelli, Terry & Wands

[57] ABSTRACT

An air/fuel ratio (A/F) sensor for detecting the A/F over a wide range covering a lean region and a rich region which are partitioned by the stoichiometric A/F comprises a solid electrolyte made of an oxygen ion conductive metal oxide, first and second electrodes sandwiching the solid electrolyte and being operable by a predetermined voltage applied thereacross to ionize oxygen near the solid electrolyte and diffuse oxygen ions into the solid electrolyte, and a gas diffusion layer in the form of a porous sintered layer covering the second electrode and made of electrically insulative metal oxide fine particles having a mean particulate size of 1 $\mu$m or less so that oxygen or molecules of other gas components in the exhaust gas can move through pores of the gas diffusion layer.

24 Claims, 7 Drawing Sheets

⊢———⊣ 5μm (x 4,000)

SENSOR FOR MEASUREMENT OF AIR/FUEL RATIO AND METHOD OF MANUFACTURING

BACKGROUND OF THE INVENTION

This invention relates to sensors for measurement of air/fuel ratio and more particularly to an air/fuel ratio measuring sensor which can detect the air/fuel ratio over a wide range covering low air/fuel ratio (rich region) and high air/fuel ratio (lean region) which are partitioned by the stoichiometric air/fuel ratio. The sensor is suitable for use in a fuel controller of an automobile engine.

In a fuel control system for automobile using an air/fuel ratio sensor, the actual air/fuel ratio in mixture gas is measured by detecting the concentration of oxygen and unburnt gases (CO, $H_2$, HC) in the exhaust gas, and information indicative of the air/fuel ratio (hereinafter abbreviated as A/F) is fed back to a fuel flow control circuit which in turn controls the fuel flow such that the mixture gas maintains a target A/F. The A/F at which gasoline fuel in mixture gas is completely burnt is known as the stoichiometric A/F which is 14.7.

As present, a stoichiometric sensor (so-called $O_2$ sensor) for detecting the stoichiometric A/F point or a lean sensor for continuously detecting the A/F over a range covering the stoichiometric A/F and the lean region is available as the A/F sensor.

Running automobiles in various ambient conditions and with widely changing loading, and therefore the A/F must be controlled adaptively over a wide range in accordance with running condition and load. For example, the A/F has to be controlled to lean A/F for light load, to rich A/F for heavy load and low temperature and to the stoichiometric A/F for a region where a 3-way catalyzer is activated.

However, technical difficulties are encountered in manufacture of a sensor which can afford to measure the A/F in a rich region because the structure of a gas diffusion layer of the sensor causes a bottleneck. The gas diffusion layer structure plays an important role in measurement of the rich A/F as will be described below with reference to FIGS. 1 to 3.

FIG. 3 shows the relation between A/F value and concentration of components in the exhaust gas. Excepting the five components shown in FIG. 3, nitrogen is predominent in the exhaust gas. In the lean region, nitrogen and oxygen are predominant as components in the exhaust gas and when compared with these components, carbon monoxide, hydrogen and hydrocarbon are contained by a very small amount in the exhaust gas. Contrarily, in the rich region, the amount of oxygen contained in the exhaust gas is small but carbon monoxide, hydrogen and hydrocarbon which stand for incompletely burnt components are predominant.

FIG. 1 shows a fragmentary section of an A/F sensor. In FIG. 1, 1 designates a solid electrolyte made of, for example, zirconia through which oxygen ions can permeate, $2a$ and $2b$ porous reaction electrodes across which a predetermined voltage V is applied, and 3 a porous gas diffusion layer made of, for example, ceramic.

In the case of the lean A/F, the oxygen concentration is higher on the exhaust gas side than on the reaction electrode $2b$ and consequently oxygen molecules move through the gas diffusion layer 3 and reach the reaction electrode $2b$ at which they are ionized. Oxygen ions $O_2^-$ than pass through the solid electrolyte 1 to reach the electrode $2a$. The amount of moving oxygen ions is detected to provide a pump current value Ip which is increased as the applied voltage increases. The gas diffusion layer 3 is so configured as to limit the diffusion speed of oxygen molecules passing through the layer 3. The diffusion speed depends on the size and number of pores present in the gas diffusion layer 3. When the diffusion speed of oxygen is properly limited, characteristics can be obtained wherein the current value Ip* is saturated over a certain voltage range as shown in FIG. 2. The saturated current value is called a diffusion limiting current value. The limiting current value changes with the A/F value. Accordingly, the A/F can be determined by detecting the limiting current Ip while keeping the voltage V constant.

In the case of the rich A/F, carbon monoxide, hydrogen and hydrocarbon which stand for incompletely burnt components in the exhaust gas diffuse through the gas diffusion layer 3. Oxygen in the atmosphere, on the other hand, is ionized while passing through the electrode $2a$, and the oxygen ions move through the solid electrolyte 1 and combine with the carbon monoxide, hydrogen and hydrocarbon. Since the size of the molecule of the incompletely burnt components is far smaller than that of an oxygen molecule, the gas diffusion layer having ability to properly limit the diffusion speed of oxygen molecule can not limit the diffusion speeds of the incompletely burnt components, with the result that excessive amounts of incompletely burnt components migrate to the electrode $2b$. On the other hand, the diffusion speed of oxygen prevailing on the atmosphere side is limited by a flow path resistance between the outer cap housing the sensor and the solid electrolyte. Further, because of low temperatures near the electrode $2b$, oxidation (combustion) reaction of incompletely burnt components with ionized oxygen ($O_2^-$) at the electrode $2b$ is insufficient, thus preventing complete combustion. Accordingly, limiting current characteristics for the rich A/F can not be obtained and the rich A/F can not be detected. In order to realize detection of the rich A/F, the flow of excessive amounts of incompletely burnt components must be suppressed to decrease absolute value of the limiting current Ip*. To this end, a gas diffusion layer capable of limiting the diffusion speed of the incompletely burnt components is needed.

As well known in the art, the diffusion limiting current Ip* is expressed by the following theoretical formula (1):

$$Ip^* = \frac{4F}{RT} \frac{S}{l} \sum_i \alpha_i D_i P_i \qquad (1)$$

where
F: Faraday constant
R: gas constant
T: aboslute temperature of gas
S: equivalent sectional area of pores in the gas diffusion layer
l: thickness of the gas diffusion layer
$\alpha_i$: conversion constant
$D_i$: diffusion coefficient of molecules
$p_i$: partial pressure of gas.

The values of the limiting currents shown in FIG. 2 are determined by inserting values of constants and variables into equation (1). By unifying the constants, equation (1) can be reduced to equation (2), $$Ip^* = K \cdot \frac{S}{l} \tag{2}$$

where K: constant.

As is clear from equation (2), the limiting current $Ip^*$ is determined by the equivalent sectional area S of pores representative of the denseness of the gas diffusion layer and the thickness l of the gas diffusion layer.

As the thickness l of the gas diffusion layer increases, the limiting current $Ip^*$ decreases. But an excessively large thickness affects response speed and durability and therefore there exists an upper limit of the thickness. Accordingly, the limiting current $Ip^*$ essentially depends on the equivalent sectional area S of pores of the gas diffusion layer. The smaller the equivalent sectional area S, that is, the denser the gas diffusion layer, the smaller the limiting current $Ip^*$ becomes to meet effective detection control in the rich region.

A conventional stoichiometric sensor ($O_2$ sensor) is disclosed in, for example, JP-A-13980 published on Feb. 8, 1978 which corresponds to a Japanese patent application by Suzuki et al filed July 23, 1976. The sensor in this literature has a gas diffusion layer prepared through plasma spraying process. The gas diffusion layer has a two-layer structure in which two layers have different thicknesses, with the outer layer closer to the exhaust gas having a thickness of 80 μm and larger pores and the inner layer closer to the solid electrolyte having a thickness of 30 μm and smaller pores.

A lean sensor is disclosed in, for example, U.S. Pat. No. 4,356,065 to Dietz issued Oct. 26, 1982. The patented sensor has a gas diffusion layer of a two-layer structure prepared through plasma spraying process. The thickness of a first layer having larger pores is 300 μm and the thickness of a second inner layer having smaller pores is 2 nm.

The gas diffusion layers of the two known sensors are prepared through plasma spraying process. The plasma spraying process is one of excellent methods for formation of porous films but is disadvantageous in that:

(1) A prepared layer inevitably has a relatively large thickness and accordingly its response speed is poor and also weak in thermal stress in the operation;

(2) During spraying, the material is exposed to high temperatuers and cracks due to thermal stress tend to occur in the layer;

(3) Many sensors can not be manufactured at a time; and (4) The manufacture cost is high.

Another sensor is known which does not rely on plasma spraying but uses a sintered material of superfine particles. This sensor corresponds to, for example, a gas sensor using superfine tin oxide particles described in National Technical Report, Vol. 26 (1980), page 457. The sintered material takes advantage of the fact that the surfaces of superfine particles are very active and highly adsorptive for gases, and is used as a solid electrolyte. However, this literature never teaches that the sintered material can be utilized for limitation of the diffusion speed of gases in the gas diffusion layer of the A/F sensor, such limitation being the task of the present invention, and the operation of the sintered material essentially differs from that of the gas diffusion layer of the A/F sensor.

In the past, superfine particles have also been used for a partition film for gas separation, as exemplified in "KOGYOZAIRYO", vol. 31, No. 7 (1983), page 50. The partition film for gas separation is adapted to extract a desired gas component from a mixture gas. This literature describes that gas separation takes advantage of the fact that when gases pass through a space whose size is smaller than a mean free path of the gases, the diffusion coefficient of the gases depends on the size of the space.

Exchangeability does not exist between this partition film for gas separation and the gas diffusion layer of A/F sensor to which the present invention pertains and the two are quite different from each other. While the pore diameter of the gas-separation partition film is 100 Å or less, the pore diameter of the gas diffusion layer of A/F sensor to which the invention pertains measures 200 to 500 Å. The gas-separation partition film is used in clean environments at room temperature but the A/F sensor is used in polluted envirnments at high temperatures. The former is applicable to selection of gas but the latter is applied to control of the speed of gas flow. Especially, because of different pore diameters, the partition film and the gas diffusion layer operate quite differently as will be described below.

When gases diffuse through pores, the gas flow takes the form of a molecular flow if a pore has a diameter smaller than a mean free path of the gases and the molecular flow has a diffusion coefficient $D_A$ indicated by, $$D_A = 9.7 \times 10^3 d \, (T/M_A)^{0.5} \tag{3}$$

where
d: pore diameter
T: temperature
$M_A$: molecular weight of A component molecule.

On the other hand, if the pore diameter is larger than the mean free path of the gases, the gas flow takes the form of a viscous flow having its diffusion coefficient $D_{AB}$ which is given by, $$D_{AB} = \frac{10^{-3} T^{1.75}(1/M_A + 1/M_B)}{P(V_A^{\frac{1}{3}} + V_B^{\frac{1}{3}})} \tag{4}$$

where
P: gas pressure
$V_A$: molecular volume of A component molecule.

By substituting equations (3) and (4) into the previous equation (1), the diffusion limiting current for the molecular flow is, $$Ip^* = C_1 \frac{P_A}{T^{0.5}} \cdot \frac{S}{l} \tag{5}$$

where
$C_1$: constant
$P_A$: partial pressure of A component molecule
and the limiting current for the viscous flow is, $$Ip^* = C_2 \, T^{0.75} \frac{P_A}{P} \cdot \frac{S}{l} \tag{6}$$

where $C_2$: constant.

Thus, equations (5) and (6) demonstrate that dependency of the limiting current upon temperatures exhibits counter positive and negative correlations in accordance with the relation in magnitude between the pore diameter and the mean free path of the gases. In particular, when the pore diameter nearly equals the gas mean free path, the gas flow takes the form of a medium flow between the molecular and viscous flows and the limiting current becomes substantially unchangeable with temperature.

Because of a difference in pore diameter, the gas flow in the gas-separation partition film takes the form of a molecular flow but the gas flow in the gas diffusion layer takes the form of a medium flow. Accordingly, the output of a sensor using the gas diffusion layer depends on temperatures very little and this sensor is suitable for use as an A/F sensor. However, in contrast, since the output of a sensor using the gas-separation partition film remarkably depends on temperatures, this sensor is unsuitable for use as an A/F sensor.

SUMMARY OF THE INVENTION

An object of this invention is to provide an A/F sensor capable of measuring the rich A/F and which is not manufactured through plasma spraying process and a method of manufacturing the same.

According to the invention, there is provided an A/F sensor having a dense gas diffusion layer in the form of a thin coating having small-diameter pores which is prepared by sintering electrically insulative metallic superfine particles having a mean particle size of 1 μm or less in order to meet the aforementioned conditions required for detection of the rich region.

In accordance with an embodiment of the invention, the mean diameter of pores of the gas diffusion layer is changed in the direction of the layer thickness.

In accordance with another embodiment of the invention, the gas diffusion layer has a two-layer structure in which two layers have different porosity values and the thickness of one layer having greater number of pores is larger with the thickness of the other layer having smaller number of pores.

In accordance with another embodiment of the invention, the gas diffusion layer has a multi-layer structure in which a plurality of layers have pores of different mean diameters, and electrically insulative metal oxide particles having a mean particle size of 1 μm or less are sintered to form a layer of the maximum pore diameter and electrically insulative metal oxide particles having a mean particle size of 0.1 μm or less are sintered to form a layer of the minimum pore diameter.

In accordance with another embodiment of the invention, the gas diffusion layer has a multi-layer structure in which a plurality of layers have different porosity values and a layer having the maximum number of pores is formed on the outer surface of a reaction electrode and a layer having the minimum number of pores is laminated on or impregnated in the outer surface of the layer having the maximum number of pores.

In a method of manufacturing a sensor according to the invention, fine particles of electrically insulative metal oxide having a mean particle size of 1 μm or less are dispersed in a liquid to form a dispersion liquid, the dispersion liquid is coated on the surface of an outer electrode attached to a solid electrolyte to form a coating, and the coating is dried and sintered to form a gas diffusion layer.

The gas diffusion layer of an A/F sensor prepared in accordance with the invention by sintering fine particles of 1 μm or less mean particle size without resort to the plasma spraying process can be a very thin diffusion layer having a small pore diameter which can properly limit the diffusion speed of incompletely burnt components to permit measurement of A/F in the rich region.

The present invention features an A/F sensor which is robust to thermal stress and highly durable. The invention also features products which can be manufactured at a low cost and at a high yield.

DESCRIPTION OF THE PREFERRED EMBODIMENTS

Figure 1:
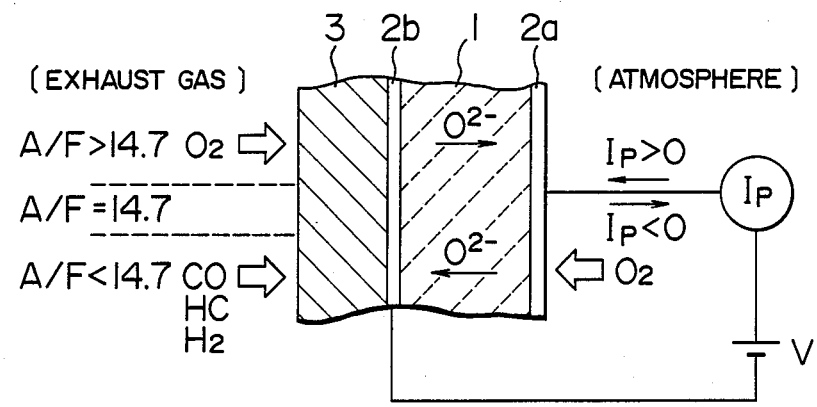
FIG. 1 is an enlarged fragmentary view of an A/F sensor useful in explaining the principle of the sensor.
Figure 2:
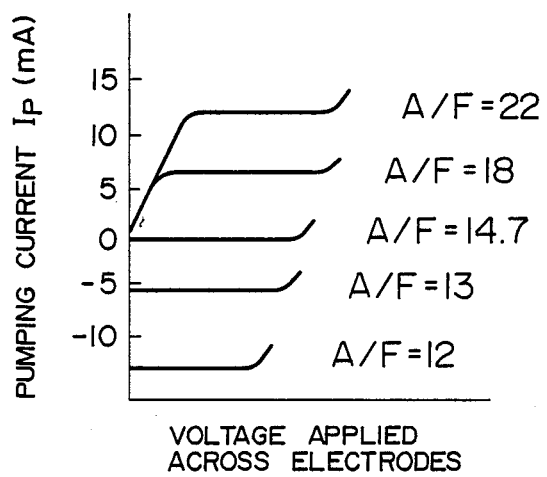
FIG. 2 is a graph showing diffusion limiting current characteristics for various A/F values in the A/F sensor.
Figure 3:
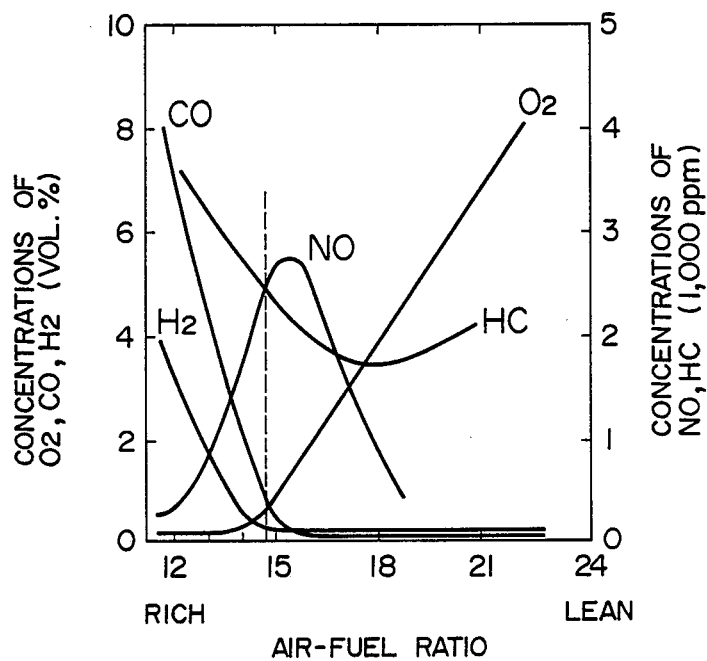
FIG. 3 is a graph showing the relation between the A/F of a mixture gas and the concentration of components in exhaust gas.
Figure 4:
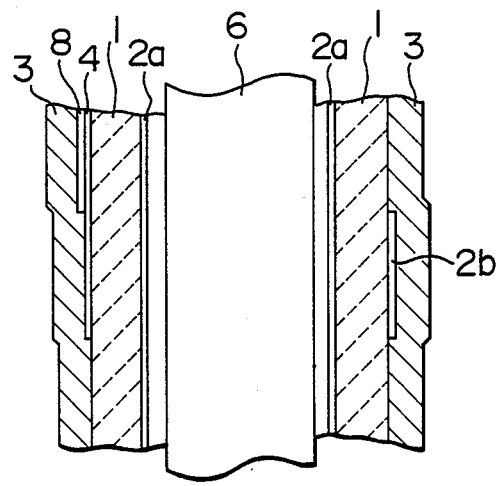
FIG. 4 is an enlarged fragmentary view illustrating the construction of an A/F sensor according to an embodiment of the invention.

FIG. 4 illustrates, in sectional form, the essential part of a gas diffusion layer of a sensor for measurement of A/F according to an embodiment of the invention and the sensor is used for feedback control of A/F in automobiles.

Referring to FIG. 4, a solid electrolyte element (hereinafter simply referred to as a solid electrolyte) is made of an oxygen ion conductive metaloxide, especially in this example, zirconium oxide (zirconia) which is partly stabilized by adding to zirconia yttrium oxide (yttria) taking the form of a solid solution in the zirconia. Platinum is plated on the inner and outer surfaces of the solid electrolyte 1 to form porous thin films of reaction electrodes 2a and 2b. Since the outer reaction electrode 2b is related to the pore sectional area S in the previously-described theoretical formula (1) which affects the characteristic, this electrode is formed with high dimensional accuracy by covering the surface not to be plated with a mask when plating platinum. A gas diffusion layer 3 made of an electrically insulative metal oxide covers the outer reaction electrode 2b. Denoted by 4 is a lead electrode and 6 a heater adapted to heat the solid electrolyte 1.

The lead electrode 4 connected to the outer reaction electrode 2b is formed by plating platinum while being masked simultaneously with the electrode 2b. Further, the lead electrode 4 is covered with a dense glass insulating layer 8 so as to be completely shielded from reaction with the exhaust gas. Superfine particles are sintered to form the gas diffusion layer 3 which covers the outer surface of the insulating layer 8. Preferably, used as a material of the superfine particles is zirconia partly stabilized by yytria or magnesia spinel having the almost same thermal expansion coefficient as that of the material of the solid electrolyte 1.

Figure 5:
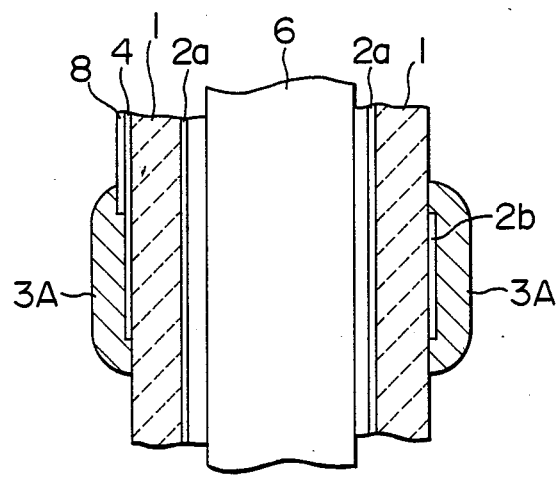
FIG. 5 is a similar view of an A/F sensor according to another embodiment of the invention.

FIG. 5 illustrates, in sectional form, the essential part of a gas diffusion layer of A/F measuring sensor according to another embodiment of the invention. In FIG. 5, elements like those of FIG. 4 are designated by like reference characters and will not be described herein.

In comparison with the FIG. 4 embodiment, a gas diffusion layer 3A of the FIG. 5 embodiment is configured differently from the layer 3. The gas diffusion layer is not always required to cover the entire outer surface of the solid electrolyte 1 and the gas diffusion layer 3A covering at least the entire surface of the outer reaction electrode 2b in accordance with the present embodiment is well adapted for the object.

The sintered coating of superfine particles used in the embodiments of FIGS. 4 and 5 will now be described specifically.

It is recommended that the mean particulate size of superfine particles used in the present invention be 1 $\mu$m or less.

Firstly, particles of zirconia partly stabilized by yttria (or magnesia spinel), preferably having a mean particulate size of 0.3 to 0.5 $\mu$m are mixed with water containing suitable peptizator and binder and dispersed for more than 18 hours by using a ball mill. A semi-finished device is dipped in the thus prepared dispersion liquid, dried with air and then sintered at around 1,300° ~ 1,500° C. for one hour. This sintering temperature is relatively lower than the temperature for production of general ceramics which ranges from 1,800° C. to 1,900° C. Through the above process a film having a thickness of about 50 $\mu$m can be prepared. For coating of the dispersion liquid, other methods than dipping may be employed including brushing, spraying, spin coating and blading. In this manner, a gas diffusion layer having diffusion speed limiting ability necessary for detection of the rich A/F can be obtained.

Figure 6:
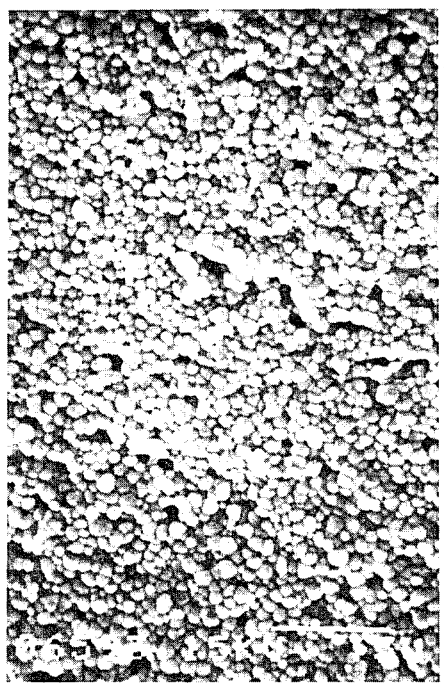
FIG. 6 shows an electron microscopic photograph of a gas diffusion layer of the A/F sensor according to the invention.

FIG. 6 shows an electron microscopic photograph (4,000 magnifications) of the surface of the sintered layer of zirconia partly stabilized by yttria.

The photograph demonstrates that crystal particles become slightly larger than the material particles becomes slightly larger than the material particles so as to have a particulate size of a little less than 1 $\mu$m, thereby proving that sintering has proceeded. Exhaust gas components can diffuse through pores observed as black points in FIG. 6.

In the embodiments of FIGS. 4 and 5, the gas diffusion layer is of a single layer structure but it is more preferable that the size of pores of the layer be changed in the direction of thickness of the layer.

Figure 7:
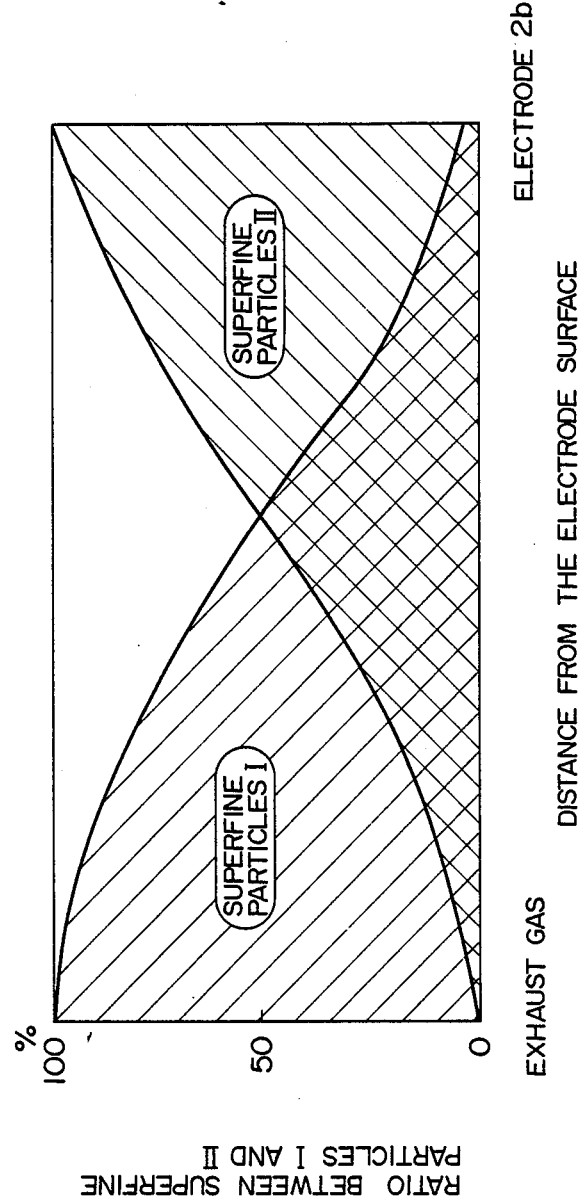
FIG. 7 is a graphical representation useful in explaining a two-layer structure of the gas diffusion layer.

FIG. 7 shows distributions of two kinds of superfine particles over the distance ranging from the interior adjacent the electrode to the outer surface. It will be appreciated that the distributions of the two kinds of superfine particles change continuously in the direction of thickness of the gas diffusion layer and accordingly denseness of the layer changes also continuously. Specifically, a first gas diffusion layer of superfine particle I corresponds to the sintered superfine-particle coating of zirconia partly stabilized by yttria.

In particular, a layer of particles having relatively large particle size is formed on the outer surface of the electrode 2b. Subsequently, a semifinished device is dipped in or coated with a dispersion liquid containing silica or zirconia particles having a mean particulate size of 0.1 $\mu$m or less (for example, 0.02 $\mu$m) to permit the superfine particles having the very small particle size to permeate into pores of the layer of large particle size, is then dried and thereafter sintered at around 700° C.~900° C. for 30 minutes. Through the above process, the superfine particles of an outer layer permeate into pores of an inner layer and denseness of the overall gas diffusion layer can be changed continuously in the direction of the overall thickness.

Figure 8:
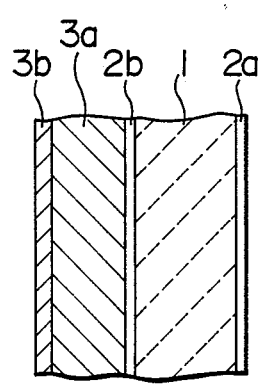
FIGS. 8 to 12 are enlarged fragmentary views illustrating the construction of A/F sensors according to further embodiments of the invention.

FIG. 8 illustrates, in sectional form, the essential part of a composite structure of the gas diffusion layer. In FIG. 8, elements like those of FIG. 4 are designated by like reference characters.

Referring to FIG. 8, a first gas diffusion layer 3a is formed on the outer reaction electrode 2b by coating superfine particles of zirconia partly stabilized by yttria. It is important that the first gas diffusion layer 3a be relatively rough. The denseness of this layer, which has close relation to catalytic reaction on the electrode, must be determined properly to permit the sensor to have good response speed. For example, by estimation, the porosity as measured by a mercury porosimeter is about 5 to 10% or the mean pore size is 300 to 400 Å.

The thickness of the first gas diffusion layer 3a is 200 $\mu$m or less and with an unnecessarily large thickness, cracks due to difference in thermal expansion coefficient between the solid electrolyte 1 and the layer 3a tend to occur, leading to degradation of response speed. Accordingly, the thickness of the first as diffusion layer 3a is preferably 100 $\mu$m or less. A second gas diffusion layer 3b is formed on the first gas diffusion layer 3a by coating sintered superfine particles. Particularly, in detecting low A/F values in the rich region, the second layer conveniently functions to limit the diffusion speed of fine gas molecules such as CO, $H_2$ and HC which stand for incompletely burnt gas components. With an excessively large thickness of the second gas diffusion layer, the gas diffusion is difficult to take place and therefore the thickness is 0.01 to 20 $\mu$m, preferably, 0.01 to 5 $\mu$m.

To prepare the second gas diffusion layer 3b, an organic solvent containing silica particles or zirconia particles having a mean particulate size of 0.1 $\mu$m or less (for example, 0.02 $\mu$m) is coated on the first gas diffusion layer 3a after sintering thereof, then dried and finally sintered at 700° C. for 30 minutes. This process repeats itself twice to provide a film thickness of about 1 $\mu$m.

Through the above process, a composite gas diffusion layer can be completed which has the highly dense outer layer capable of limiting the diffusion speed of incompletely burnt gas components and the inner layer capable of permitting suitable gas diffusion and efficiently promoting the speed of reaction with the platinum electrode.

Although the composite gas diffusion layer of the FIG. 8 embodiment has a lamination structure of two distinctively separated layers, the invention may be realized with other various composite structures.

FIGS. 9 to 12 illustrate, in sectional form, the essential part of composite structures of the gas diffusion layer according to further embodiments of the invention.

Figure 9:
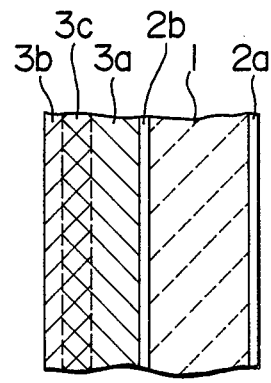

Firstly, referring to FIG. 9, this embodiment additionally has a transition gas diffusion layer 3c. Especially where the porosity of the first gas diffusion layer 3a is high and the wettability of a solvent of the second gas diffusion layer 3b is high for a material of the first gas diffusion layer 3a, the intermediate transition gas diffusion layer 3c can be provided in which the material of the second gas diffusion layer 3b are impregnated in pores of the first gas diffusion layer 3a.

Advantageously, in the FIG. 9 embodiment, even when the thermal expansion coefficient of first gas diffusion layer 3a greatly differs from that of second gas diffusion layer 3b, concentration of thermal stress can be mitigated by the transition gas diffusion layer 3c and a highly durable composite gas diffusion layer can be obtained.

Figure 10:
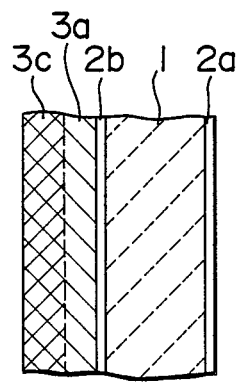

The FIG. 9 embodiment may be modified to extremities to provide an embodiment of FIG. 10 based on permeance to advantage. In the FIG. 10 embodiment, a material for formation of the second gas diffusion layer is perfectly impregnated in the first gas diffusion layer 3a to form a lamination structure of only first gas diffusion layer 3a and transition gas diffusion layer 3c.

Figure 11:
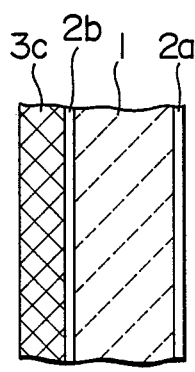

If the FIG. 10 embodiment the thickness of the first gas diffusion layer is sufficiently small, the material for formation of the second gas diffusion layer is impregnated over the entirety of the first gas diffusion layer. In this case the gas diffusion layer includes the transition gas diffusion layer 3c alone as shown in FIG. 11 and the resulting structure may be interpreted in a broad sense as a lamination structure in which components continuously change in the direction of depth. This lamination structure is of the highest durability.

Figure 12:
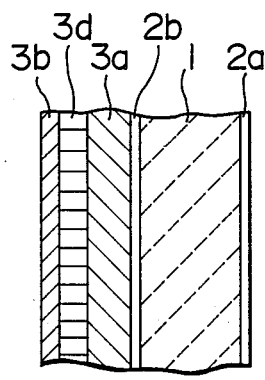

As shown in FIG. 12, it is also advantageous to provide, between the first gas diffusion layer 3a and the second gas diffusion layer 3b, a single- or multi-layer, intermediate, third gas diffusion layer 3d made of a material which is quite different from that of the first and second layers. An effective material for the intermediate gas diffusion layer 3d has a thermal expansion coefficient which lies between those of the first gas diffusion layer 3a and second gas diffusion layer 3b. In preparing this composite gas diffusion layer, the process of dipping, drying and sintering is repeated by the number of layers.

In the foregoing embodiments, the gas diffusion layer is prepared by sintering and coating superfine particles, so that the cost can be reduced and the film thickness can also be reduced to improve the durability against thermal stress and the response speed. Also, variation in characteristics can be minimized to improve the yield. Further, the rough layer of the gas diffusion layer and the solid electrolyte element body are made of the same material, i.e., zirconia partly stabilized by yttria and as a result the difference in thermal expansion coefficient can be minimized to suppress, to advantage, the generation of thermal stress.

The overall construction and output characteristic of a limiting current type A/F measuring sensor having such a gas diffusion layer as prepared in accordance with the foregoing embodiments will not be described with reference to FIGS. 13 and 14.

Figure 13:
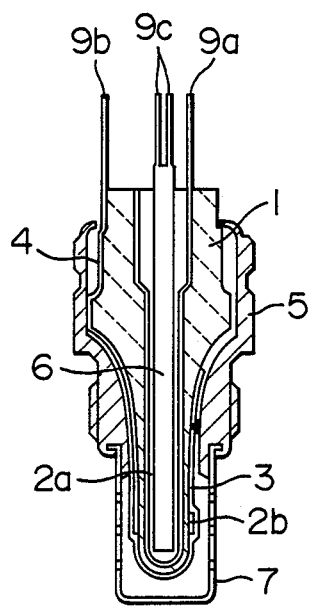
FIG. 13 is an overall sectional view of an A/F sensor to which the invention is applied.
Figure 14:
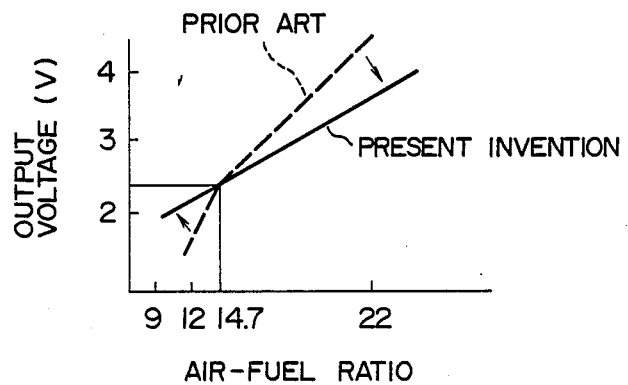
FIG. 14 is a graph showing an output characteristic of the A/F sensor according to the invention.

An embodiment of the sensor capable of exhibiting an output characteristic as shown in FIG. 14 is illustrated, in sectional form, in FIG. 13.

Referring to FIG. 13, a solid electrolyte 1 is fixedlly connected to a plug 5. The plug 5 has, at its tip, a cap 7 adapted to protect a gas diffusion layer 3 prepared in accordance with the foregoing embodiments from impurities in the exhaust gas. Disposed in the solid electrolyte 1 is a heater 6 for heating the solid electrolyte element to 600° to 700° C. so that zirconia, the material of the element, may be activated to act as an electrolyte.

For picking-up of electrical signals and application of voltage, lead wires 9a, 9b and 9c are connected to an inner reaction electrode 2a, an outer reaction electrode 2b and the heater 6, respectively.

When the thus constructed limiting current type A/F measuring sensor is mounted to the exhaust pipe of an engine and a voltage is applied across the reaction electrodes 2a and 2b while heating the solid electrolyte 1 to about 700° C. by current conduction to the heater 6, an output characteristic as represented at solid line in FIG. 14 can be obtained, indicating that the output voltage changes linearly with the A/F over the lean region, stoichiometric A/F equalling 14.7 and rich region. With the conventional gas diffusion layer, the output characteristic is abruptly decreased in the rich region where the fuel concentration is high, as represented at dotted line in FIG. 14, and the detection of the A/F in the rich region is limited by A/F=12. This advantage can be eliminated by the present embodiment of the invention.

Fuel control in an automobile engine is practiced using the above sensor, proving that normal running (40 to 60 Km/h) on the level ground is controlled in the lean region to achieve economical running, running on ascending slopes such as roads in the mountains is controlled in the rich region to provide an improved output characteristic and the running characteristic can be improved as a whole.

In an automobile engine employed with A/F feedback control system including a conventional $O_2$ sensor and 3 way catalyst, the mixture sometimes takes rich air/fuel ratio at cold start or wide throttle opening. The present invention can apply to the conventional 3 way catalyst system to control the rich A/F region thereby to improve fuel economy and drivability.

The material of zirconia particles partly stabilized by yttria used for the rough layer of the gas diffusion layer in the previous embodiments is not limitative. For example, a sintered film having a porosity of 2 to 20% measured by a mercury porosimeter or a mean particulate size of 200 to 500 Å can fulfil effects of the invention. Thus particles of ceramic such as alumina, magnesia, silica, titania or calcia or a mixture thereof may be used to advantage.

The material of silica particles used for the dense layer of the gas diffusion layer in the embodiments previously described is not limitative and obviously alumina, magnesia, titania or calcia may be used to attain the same effects.

Further, an outer rough layer may be formed on a dense layer provided on the electrode to attain similar effects.

We claim:

1. A sensor for measurement of air/fuel ratio (A/F) comprising:
    a solid electrolyte made of an oxygen ion conductive metal oxide, having an atmospheric side surface and an exhaust gas side surface;
    first and second electrodes in the form of porous thin films which are respectively provided on the atmosphere side surface and the exhaust gas side surface of said solid electrolyte, said first and second electrodes being operable by a predetermined voltage applied thereacross to ionize oxygen near said solid electrolyte and diffuse oxygen ions into said solid electrolyte; and
    a gas diffusion layer in the form of a porous sintered layer covering said second electrode and made of electrically insulative metal oxide fine particles having a mean particulate size of 1 μm or less, said gas diffusion layer having first and second porous sintered layers respectively made of two kinds of electrically insulative metal oxide fine particles having different mean particulate sizes, said first porous sintered layer being contiguous to said second electrode and having a larger mean particulate size than that of said second porous sintered layer, contiguous to the exhaust gas, the second electrically insulative metal oxide layer, contiguous to the exhaust gas, having a mean particle size which measures 0.1 μm or less, said gas diffusion layer further comprising an intermediate layer between said first and second layer, part of said second layer being impregnated into part of pores of said first layer to form said intermediate layer, so that oxygen or molecules of other gas components in the exhaust gas can move through pores of said gas diffusion layer, but that the gas diffusion layer limits diffusion speed of incompletely burnt gas components in the exhaust gas therethrough, whereby the measuring sensor can be used for a rich A/F range.

2. An A/F measuring sensor according to claim 1 wherein the mean diameter of pores of said gas diffusion layer is not higher than 400 Å when measured by a mercury porosimeter.

3. An A/F measuring sensor according to claim 2 wherein the mean diameter of pores of said gas diffusion layer is 300Å–400Å when measured by a mercury porosimeter.

4. An A/F measuring sensor according to claim 1 wherein the thickness of said second layer is smaller than that of said first layer.

5. An A/F measuring sensor according to claim 4 wherein the thickness of said first layer is 100 μm or less and the thickness of said second layer ranges from 0.1 μm to 5 μm.

6. A sensor for measurement of air/fuel ratio (A/F) comprising:
a solid electrolyte made of an oxygen ion conductive metal oxide, having an atmospheric side surface and an exhaust gas side surface;
first and second electrodes in the form of porous thin films which are respectively provided on the atmosphere side surface and the exhaust gas side surface of said solid electrolyte, said first and second electrodes being operable by a predetermined voltage applied thereacross to ionize oxygen near said solid electrolyte and diffuse oxygen ions into said solid electrolyte; and
a gas diffusion layer in the form of a porous sintered layer covering said second electrode and made of electrically insulative metal oxide fine particles having a mean particulate size of 1 μm or less, said gas diffusion layer having first and second porous sintered layers respectively made of two kinds of electrically insulative metal oxide fine particles having different mean particulate sizes, said first porous sintered layer being contiguous to said second electrode and having a larger mean particulate size than that of said second porous sintered layer, contiguous to the exhaust gas, the second electrically insulative metal oxide layer, contiguous to the exhaust gas, having a mean particle size which measures 0.1 μm or less, the entirety of said second layer being impregnated into part of pores of said first layer to form said gas diffusion layer, so that oxygen or molecules of other gas components in the exhaust gas can move through pores of said gas diffusion layer, but that the gas diffusion layer limits diffusion speed of incompletely burnt gas components in the exhaust gas therethrough, whereby the measuring sensor can be used for a rich A/F range.

7. A sensor for measurement of air/fuel ratio (A/F) comprising:
a solid electrolyte made of an oxygen ion conductive metal oxide, having an atmospheric side surface and an exhaust gas side surface;
first and second electrodes in the form of porous thin films which are respectively provided on the atmosphere side surface and the exhaust gas side surface of said solid electrolyte, said first and second electrodes being operable by a predetermined voltage applied thereacross to ionize oxygen near said solid electrolyte and diffuse oxygen ions into said solid electrolyte; and
a gas diffusion layer in the form of a porous sintered layer covering said second electrode and made of electrically insulative metal oxide fine particles having a mean particulate size of 1 μm or less, said gas diffusion layer having a plurality of porous sintered layers respectively made of two kinds of electrically insulative metal oxide fine particles having different mean particulate sizes, an electrically insulative metal oxide layer of said gas diffusion layer having smaller mean particulate size being impregnated into an electrically insulative metal oxide layer having larger mean particulate size, an electrically insulative metal oxide layer, contiguous to the exhaust gas, having an mean praticle size which is smaller than that of an electrically insulative metal oxide layer contiguous to said second electrode and which measures 0.1 μm or less, so that oxygen or molecules of other gas components in the exhaust gas can move through pores of said gas diffusion layer, but that the gas diffusion layer limits diffusion speed of incompletely burnt gas components in the exhaust gas therethrough, whereby the measuring sensor can be used for a rich A/F range.

8. An A/F measuring sensor according to claim 7 wherein the porosity of a portion of said gas diffusion layer contiguous to said second electrode ranges from 5% to 10%.

9. An A/F measuring sensor according to claim 7 wherein the porosity of said gas diffusion layer is so selected as to range not higher than 10%.

10. An A/F measuring sensor according to claim 7 wherein the mean diameter of pores of a portion of said gas diffusion layer contiguous to said second electrode is 300 to 400 Å when measured by a mercury porosimeter.

11. An A/F measuring sensor according to claim 7 wherein the gas diffusion layer is made of said fine particles, of a mean particulate size such that the gas diffusion layer limits diffusion speed of incompletely burnt gas components of CO, $H_2$ and hydrocarbon, in the exhaust gas, therethrough.

12. An A/F measuring sensor according to claim 7 wherein said second layer has a thickness of 0.01–20 μm.

13. An A/F measuring sensor according to claim 12 wherein said first layer has a thickness of 200 μm or less.

14. An A/F measuring sensor according to claim 7 wherein the gas diffusion layer covers only the entire second electrode.

15. An A/F measuring sensor according to claim 7 wherein the exhaust gas side surface of the solid electrolyte extends beyond the second electrode, and the gas diffusion layer covers the second electrode and the exhaust gas side surface extending beyond the second electrode.

16. An A/F measuring sensor according to any one of claims 8, 9, 10, 2, 4, 5 and 1, 7 wherein said gas diffusion layer has substantially the same thermal expansion coefficient as that of said solid electrolyte.

17. A method of manufacturing the gas diffusion layer of the A/F measuring sensor of claim 16, said method comprising the steps of:
preparing a dispersion liquid by dispersing said electrically insulative metal oxide fine particles, having a mean particulate size of 1 μm or less, into a liquid;
coating the dispersion liquid on said second electrode attached to said solid electrolyte to form a coated film;
drying the coated film; and
sintering said dried coated film.

18. A method of manufacturing an A/F measuring sensor according to claim 17 wherein the dried coated film is sintered at 1300° C.–1500° C.

19. An A/F measuring sensor according to any one of claims 8, 9, 10, 2, 4, 5 and 1, 7 wherein said electrically insulative metal oxide layer of said gas diffusion layer having larger mean particulate size is made of fine particles mainly containing zirconium oxide, and said electrically insualtive metal oxide layer having smaller mean particulate size is made of fine particles mainly containing one or both of silicon oxide and zirconium oxide.

20. A method of manufacturing the gas diffusion layer of the A/F measuring sensor of claim 19, said method comprising the steps of:
preparing a dispersion liquid by dispersing said electrically insulative metal oxide fine particles, having a mean particulate size of 1 μm or less, into a liquid;
coating the dispersion liquid on said second electrode attached to said solid electrolyte to form a coated film;
drying the coated film; and
sintering said dried coated film.

21. A method of manufacturing an A/F measuring sensor according to claim 20 wherein the dried coated film is sintered at 1300° C.–1500° C.

22. An A/F measuring sensor according to any one of claim 8, 9, 10, 2, 4, 5, and 1–7 wherein said electrically insulative metal oxide layer of said gas diffusion layer having larger mean particulate size is made of fine particles of magnesia spinel.

23. A method of manufacturing the gas diffusion layer of the A/F measuring sensor of claim 22, said method comprising the steps of:
preparing a dispersion liquid by dispersing said electrically insulative metal oxide fine particles, having a mean particulate size of 1 μm or less, into a liquid;
coating the dispersion liquid on said second electrode attached to said solid electrolyte to form a coated film;
drying the coated film; and
sintering said dried coated film.

24. A method of manufacturing an A/F measuring sensor according to claim 23 wherein the dried coated film is sintered at 1300° C.–1500° C.

* * * * *